(12) United States Patent
van Hal et al.

(10) Patent No.: US 6,916,963 B2
(45) Date of Patent: Jul. 12, 2005

(54) PROCESS USING WATER TOLERANT LEWIS ACIDS IN CATALYTIC HYDRATION OF ALKYLENE OXIDES TO ALKYLENE GLYCOLS

(75) Inventors: Jaap W. van Hal, Fresno, TX (US); Dorai Ramprasad, Allentown, PA (US)

(73) Assignee: Saudi Basic Industries Corporation, Riyadh (SA)

( * ) Notice: Subject to any disclaimer, the term of this patent is extended or adjusted under 35 U.S.C. 154(b) by 148 days.

(21) Appl. No.: 10/619,127

(22) Filed: Jul. 14, 2003

(65) Prior Publication Data

US 2005/0014980 A1 Jan. 20, 2005

(51) Int. Cl.$^7$ .............................................. C07C 33/26
(52) U.S. Cl. ........................ 568/811; 568/833; 568/867
(58) Field of Search ................................ 568/811, 833, 568/867

(56) References Cited

U.S. PATENT DOCUMENTS

| | | | |
|---|---|---|---|
| 4,307,256 A | 12/1981 | Cipriania et al. | |
| 4,543,430 A | 9/1985 | Falgoux et al. | |
| 4,551,566 A | * 11/1985 | Robson et al. | 568/867 |
| 4,579,982 A | * 4/1986 | Briggs et al. | 568/867 |
| 4,967,018 A | 10/1990 | Soo et al. | |
| 5,260,495 A | 11/1993 | Forkner | |
| 5,488,184 A | 1/1996 | Reman et al. | |
| 5,728,901 A | 3/1998 | Ramprasad et al. | |
| 5,770,678 A | 6/1998 | Drysdale et al. | |
| 5,874,653 A | 2/1999 | Van Kruchten | |
| 5,948,696 A | 9/1999 | Dolle, III et al. | |
| 5,990,264 A | 11/1999 | Drysdale | |
| 6,040,484 A | 3/2000 | Costantini et al. | |
| 6,111,135 A | 8/2000 | Adelman et al. | |
| 6,187,972 B1 | 2/2001 | Kawabe et al. | |
| 6,194,580 B1 | 2/2001 | Greenwald et al. | |
| 6,348,631 B1 | 2/2002 | Desmurs et al. | |
| 6,352,954 B1 | 3/2002 | Kobayashi | |
| 6,362,375 B1 | 3/2002 | Walker | |
| 6,444,857 B1 | 9/2002 | Seko et al. | |

FOREIGN PATENT DOCUMENTS

JP 56073035 A * 6/1981 ........... C07C/31/20

OTHER PUBLICATIONS

Berkessel, Applied Catalysis A: General, vol. 254, pp. 27–34 (2003).*
"Indium Triflate: An Efficient Catalyst for the Friedel–Crafts Acylation of Aromatics", C.G. Frost et al., Fourth International Electronic Conference on Synthetic Organic. Chemistry (ECSOC–4), www.mdpi.org/ecsoc–4.htm, Sep. 1–30, 2000 (uploaded Aug. 3, 2000).
"Bismuth(III) Chloride and Triflate—Novel Catalysts for Arylation and Sulphonation Reactions—Review", Le Roux C et al, SynLett, 2002, 181.
"The Search for Larger and More Weakly Coordinating Anions", S. H. Strauss, Chem. Rev., vol. 93, p. 927–942 (1993).
"Structure and Characterization of CI3+[Al{OC(CF3)3}4]−; Lewis Acidities of CX3+ and BX3", I. Krossing et al., Angew. Chem. Int. Ed., vol. 42, p. 1531–1534 (2003).

* cited by examiner

*Primary Examiner*—Michael L. Shippen
(74) *Attorney, Agent, or Firm*—Jim Wheelington

(57) ABSTRACT

Water tolerant Lewis acids are used in a process for the preparation of alkylene glycols by catalytic hydration of the corresponding alkylene oxide. The water tolerant Lewis acids can be a metal salt of a non-coordinating or weakly coordinating anion and a Group IIIB, rare earth or lanthanide, actinide or Group IVB cation. Optionally, carbon oxide may also be present. Examples of such water tolerant Lewis acids are scandium triflate, europium triflate, hafnium triflate, yttrium triflate, lanthanum triflate and ytterbium triflate. The catalyst may contain a coordinating anion instead, examples of which are scandium sulfate [$Sc_2(SO_4)_3$], scandium chloride [$ScCl_3$], scandium acetate [$Sc(OAc)_3$] and scandium nitrate [$Sc(NO_3)_3$]. The catalysts may also contain both a non-coordinating or weakly coordinating anion and a coordinating anion, examples of which are scandium triflate sulfate [$Sc(CF_3SO_3)(SO_4)$], scandium triflate chloride [$Sc(CF_3SO_3)_2Cl$], scandium triflate acetate [$Sc(CF_3SO_3)_2(OAc)$] and scandium triflate nitrate [$Sc(CF_3SO_3)_2(NO_3)$].

32 Claims, No Drawings

PROCESS USING WATER TOLERANT LEWIS ACIDS IN CATALYTIC HYDRATION OF ALKYLENE OXIDES TO ALKYLENE GLYCOLS

BACKGROUND OF THE INVENTION

1. Field of the Invention

This invention relates to a process for the preparation of alkylene glycols by catalytic hydration of the corresponding alkylene oxide.

2. Description of the Prior Art

The production of alkylene glycols from alkylene oxides is known and is practiced commercially. Of particular interest is the production of ethylene glycol from ethylene oxide. The thermal hydration of ethylene oxide in water produces monoethylene glycol (MEG) which is used as a base material in the production of poly(ethylene terephalate) or PET which can be used to make polyester fibers, resins, films and bottles. MEG is also as a major active component in antifreeze.

Hydration of ethylene oxide can be through catalytic and non-catalytic means. Non-catalytic hydration of ethylene oxide to MEG requires a large excess of water to inhibit the formation of diethylene glycol (DEG) and other higher glycols. Even with a large excess of water the molar selectivity to MEG is only about 88%. In addition, the water must be distilled from the glycol to obtain a high purity product. Distillation is a very energy intensive process.

Catalytic hydration of ethylene oxide may use smaller amounts of water and can be carried out at lower temperatures and pressures. There are numerous examples of catalysts for hydration of an alkylene oxide to alkylene glycol.

U.S. Pat. No. 5,260,495 discloses a process for producing monoalkylene glycol with a metalate-substituted hydrotalcite composition in which an anionic clay of metal oxide/hydroxide layers with large organic anion interstitial spacers has some of these spacers replaced with a metalate anion.

U.S. Pat. No. 5,874,653 discloses a process for preparing an alkylene glycol by reaction alkylene oxide with water in the presence of a catalyst of a polymeric organosiloxane ammonium salt as an ion exchange resin catalyst.

U.S. Pat. No. 4,967,018 discloses a process for catalytic hydrolysis or alkylene oxide to alkylene glycol with a mixed metal framework catalyst of a divalent metal cation, such as magnesium, calcium, titanium, vanadium, chromium, manganese, iron, cobalt, nickel, palladium, platinum, copper, zinc, cadmium, mercury, tin and lead; a trivalent metal cation, such as aluminum, antimony, titanium, scandium, bismuth, vanadium, yttrium, chromium, iron, manganese, cobalt, ruthenium, nickel, gold, gallium, thallium and cerium; and an anion, such as halide, nitrite, nitrate, sulfite, sulfate, sulfonate, carbonate, chromate, cyanate, phosphite, phosphate, molybdocyanate, bicarbonate, hydroxide, arsenate, chlorate, ferrocyanide, borate, cyanide, cyanaurate, cyanaurite, ferricyanide, selenate, tellurate, bisulfate, oxalate, acetate, hexanoate, sebacate, formate, benzoate, malonate, lactate, oleate, salicylate, stearate, citrate, tartrate and maleate.

U.S. Pat. No. 5,488,184 discloses a process for preparation of alkylene glycols by reacting an alkylene oxide with water in the presence of a catalyst of a solid material having electropositive sites, such as silica, silica-alumina, clay, zeolite and ion-exchange resin, coordinated with an anion, such as bicarbonate, bisulfite, phosphate and carboxylate.

U.S. Pat. No. 6,187,972 discloses a process for producing an alkylene glycol from an alkylene oxide and carbon dioxide via the intermediate formation of ethylene carbonate with a catalyst of an alkali metal bromide or iodide, an alkaline earth metal bromide or iodide, an ammonium halide, such as tributyl methylammonium iodide, or a phosphonium halide, such as tributylmethylphosphonium iodide.

U.S. Pat. No. 4,307,256 discloses a process for producing alkylene glycols from alkylene oxides, water and carbon dioxide in the presence of an organic base catalyst, such as triethylamine, dimethylaniline and pyridine.

An acceptable hydration catalyst would have high selectivity to the monoalkylene glycol and a decrease in the amount of water required in comparison with a non-catalytic process. However, prior art catalysts can have problems which make their use disadvantageous. Soluble acid catalysts have corrosion problems. Alkaline catalysts have lower selectivity to MEG. Alkali metal or ammonium halides have lower solubility and are likely to precipitate which causes scaling and corrosion problems. Amine-based catalyst can have a strong, undesirable odor which can cause quality problems with the product. Ion exchange resins can result in metallate salts in the glycol product or can require long residence times. The ion exchange resins may also swell during the reaction and have limited tolerance to heat.

Ordinary Lewis acid catalysts are water sensitive and can be hydrolyzed by water. However, some Lewis acids, such as rare earth (lanthanide) triflates, are water tolerant and can be used in a variety of chemical reactions.

Indium triflate is used with lithium perchlorate in the catalytic acylation of aromatics to aromatic ketones ("Indium triflate: An Efficient Catalyst for the Friedel-Crafts Acylation of Aromatics", Christopher G. Frost and Joseph P. Hartley, Fourth International Electronic Conference on Synthetic Organic Chemistry (ECSOC-4), Aug. 3, 2000).

Bismuth triflate is used for acylation of aromatics and alcohols and the sulphonation of aromatics ("Bismuth(III) Chloride and Triflate—Novel Catalysts for Arylation and Sulphonation Reactions—Review", Le Roux C et al, SynLett, 2002, 181).

U.S. Pat. No. 6,444,857 discloses reacting an alcohol with a diol derivative in the presence of an acid catalyst, such as scandium triflate, to form an intermediate in a process for producing Vitamin A.

U.S. Pat. No. 6,362,375 discloses metal triflate catalysts to catalyze a reaction between carboxylic acid and an aromatic in the presence of a volatile organic compound which forms an azeotrope with water, such as toluene, to produce aryl ketones.

U.S. Pat. No. 6,352,954 discloses a Lewis acid, such as scandium triflate, encapsulated in a network of polymer gel which can be used in a variety of organic syntheses, such as imino-aldo condensation, Mannich-type reactions, Michael reactions and Friedel-crafts reactions.

U.S. Pat. No. 6,348,631 discloses acylation or sulphonation of aromatics to aromatic ketones or sulphones with a Lewis acid, such as a rare earth triflate.

U.S. Pat. No. 6,194,580 discloses forming esters of tertiary alcohols by reacting a compound containing a tertiary alcohol with a acyl heteroaromatic ion-based compound in the presence of a lanthanide metal based catalyst such as scandium triflate.

U.S. Pat. No. 6,111,135 discloses reacting ethylene, paraformaldehyde, formic acid and scandium triflate to form 1,3 propanediol diformate ester.

U.S. Pat. No. 6,040,484 discloses hydroxylation of phenolic compounds with hydrogen peroxide with scandium triflate.

U.S. Pat. No. 5,990,264 discloses copolymerization of tetrahydrofuran with cyclic carboxylic anhydride with scandium triflate.

U.S. Pat. No. 5,948,696 discloses an aldol reaction of treating a resin-bound aldehyde or its imine with silyl enol ether in the presence of scandium triflate in dichloromethane.

U.S. Pat. No. 5,770,678 discloses polymerization of cyclic ether, such as tetrahydrofuran, using metal compounds, such as scandium triflate and acetyl chloride or acetic anhydride.

U.S. Pat. No. 5,728,901 discloses a process for nitrating an arene with nitric acid in the presence of a catalyst, such as scandium triflate.

U.S. Pat. No. 4,543,430 discloses a process for the preparation of addition products of epoxides and hydroxylated compounds in the presence of a catalyst of a salt of trifluoromethanesulfphonic acid, such as a triflate of an alkali (Group I) metal, an alkaline earth (Group II) metal or heavy metal. The examples used aluminum triflate as the preferred catalyst. Lithium triflate was also disclosed as a catalyst.

It would be advantageous to have a catalyst for hydration of an alkylene oxide to the corresponding alkylene glycol without the disadvantages of prior art catalysts.

SUMMARY OF THE INVENTION

This invention concerns preparation of alkylene glycols from the corresponding alkylene oxides in the presence of water and a catalyst containing water tolerant Lewis acids, such as metal salts of general formula $MA_x$ wherein A is a non-coordinating or weakly coordinating anion and M is a metal with x being the valence of M. Optionally, carbon oxide may also be present. Examples of the metal include Group IIIB, rare earth or lanthanides, actinides and Group IVB. Examples of a non-coordinating or weakly coordinating anion are perfluoroalkylsulfonate, fluoralkylsulfonate and hexafluorophosphate ($[PF_6]^-$). Examples of perfluoroalkylsulfonates are trifluoromethanesulfonates ($[CF_3SO_3]^-$), also known as triflates. Examples of water tolerant Lewis acids are scandium triflate, europium triflate, hafnium triflate, yttrium triflate, lanthanum triflate and ytterbium triflate.

This invention relates in part to water tolerant Lewis acids in which the anion is non-coordinating or weakly coordinating. However, it has also been found that water tolerant Lewis acids in which the anion is coordinating, i.e., the anion is bound to the metal in an aqueous solution, are effective as catalysts for preparation of alkylene glycols from the corresponding alkylene oxides. Similar to those catalysts with a non-coordinating or weakly coordinating anion, catalysts of the formula $M'B_x$ wherein M' is a metal, B is a coordinating anion and x is the valence of M' can have a Group IIIB, rare earth or lanthanide, actinide or Group IVB cation. Examples of coordinating anions are sulfate, chloride, acetate and nitrate. Specific water tolerant Lewis acids in which the anion is coordinating are scandium sulfate $[Sc_2(SO_4)_3]$, scandium chloride $[ScCl_3]$, scandium acetate $[Sc(OAc)_3]$ and scandium nitrate $[Sc(NO_3)_3]$. While such catalysts are effective in the preparation of alkylene glycols from the corresponding alkylene oxides, the conversion and reaction time are typically not as advantageous as that for water tolerant Lewis acids in which the anion is non-coordinating or weakly coordinating.

It is expected that water tolerant Lewis acids which contain both a non-coordinating or weakly coordinating anion and a coordinating anion would be effective as catalysts for preparation of alkylene glycols from the corresponding alkylene oxides. Similar to those catalysts with a non-coordinating or weakly coordinating anion, catalysts of the formula $M''A_xB_y$ wherein M'' is a metal, A is a non-coordinating or weakly coordinating anion, B is a coordinating anion and x+y equals the valence of M'' can have a Group IIIB, rare earth or lanthanide, actinide or Group IVB cation. Specific water tolerant Lewis acids which contain both non-coordinating or weakly coordinating anions and coordinating anions are scandium triflate sulfate [Sc($CF_3SO_3$)($SO_4$)], scandium triflate chloride [Sc($CF_3SO_3$)$_2$Cl], scandium triflate acetate [Sc($CF_3SO_3$)$_2$(OAc)] and scandium triflate nitrate [Sc($CF_3SO_3$)$_2$($NO_3$)]. While such catalysts should be effective in the preparation of alkylene glycols from the corresponding alkylene oxides, the conversion and reaction time would not be expected to be as advantageous as that for water tolerant Lewis acids in which the anion is non-coordinating or weakly coordinating.

DETAILED DESCRIPTION OF THE INVENTION

Alkylene glycols can be obtained by reacting the corresponding alkylene oxide with water in the presence of a catalyst. Carbon dioxide may be added to the reaction medium to improve selectivity to the glycol.

Alkylene oxides are generally of the formula $R^1R^2(COC)R^3R^4$, where each $R^1$, $R^2$, $R^3$ and $R^4$ is independently hydrogen or an alkyl of from 1 to 10 carbon atoms. Examples of alkylene oxides are ethylene oxide, propylene oxide and butylene oxide. The corresponding alkylene glycol is generally of the formula $R^1R^2(COHCOH)R^3R^4$, where $R^1$, $R^2$, $R^3$ and $R^4$ are as defined above, and may be obtained by hydration of the alkylene oxide, i.e., reacting it with water to introduce a hydroxyl group and hydrogenate or protonate the oxygen. A mixture of glycols is formed (monoalkylene glycol, dialkylene glycol and higher alkylene glycols).

Though the reaction of alkylene oxide and water to alkylene glycol proceeds non-catalytically, improvements in reaction rate, selectivity and/or reduced water can be realized by the use of catalysts. The catalysts of the present invention are water tolerant Lewis acids, such as a metal salt catalyst of general formula $MA_x$ wherein A is a non-coordinating or weakly coordinating anion and M is a Group IIIB, rare earth or lanthanide, actinide or Group IVB cation with x being the valence of M. By the term "water-tolerant" it is meant that the Lewis acid is not hydrolyzed by water. By the term "non-coordinating or weakly coordinating anion" it is meant that the anion is not bound to the metal in an aqueous solution. Examples of a non-coordinating or weakly coordinating anion in the present inventions are trifluoromethane sulfonate, also known as triflate ($[CF_3SO_3]^-$), hexafluorophosphate ($[PF_6]^-$), $[Al[OC(CF_3)_3]_4]^-$, tetrafluoroborate ($[BF_4]^-$), perchlorate ($[ClO_4]^-$), teflate ($[TeOF_5]^-$), BArF $[B(ArH_xF_y)_4]^-$ where Ar is an aryl and x+y=5, e.g., $[B(C_6F_5)_4]^-$, tosylate ($[CH_3C_6H_4SO_3]^-$), mesylate ($[CH_3SO_3]^-$) and antimonyhexafluoride ($[SbF_6]^-$). Further examples of non-coordinating or weakly coordinating anions are found in "The Search for Larger and More Weakly Coordinating Anions", Steven H. Strauss, Chem. Rev. vol. 93, p. 927–942 (1993) and "Structure and Characterization of $Cl_3^+[Al\{OC(CF_3)_3\}]^-$; Lewis Acidities of $CX_3^+$ and $BX_3$", Ingo Krossing et al., Angew. Chem. Int. Ed., vol. 42, p. 1531–1534 (2003), which are incorporated by reference.

It should be noted that whether a particular anion is "non-coordinating or weakly coordinating" is dependent on its environment, e.g., solvent, presence of impurities and, especially, the cation. For example, sodium chloride (NaCl) is completely dissociated in water and the chlorine anion would be a non-coordinating or weakly coordinating anion; however, aluminum chloride ($AlCl_3$) in an aqueous solution would still have chloride ions bound to the metal and chloride would not be non-coordinating or weakly coordinating.

Examples of Group IIIB metals are scandium and yttrium. An example of Group IVB metal is hafnium. Examples of rare earth or lanthanide cation are lanthanum, europium and ytterbium. Examples of water tolerant Lewis acids in the present invention are scandium triflate [$Sc(CF_3SO_3)_3$], europium triflate [$Eu(CF_3SO_3)_3$], hafnium triflate [$Hf(CF_3SO_3)_4$], yttrium triflate [$Y(CF_3SO_3)_3$], lanthanum triflate [$La(CF_3SO_3)_3$] and ytterbium triflate [$Yb(CF_3SO_3)_3$]. Many of these water tolerant Lewis acids are commercially available or can be synthesized by methods known in the art.

The catalysts of the present invention are typically homogeneous, i.e., liquid phase. The catalysts may be heterogenized using procedures known in the art. These procedures include the use of ion exchange resins, microencapsulation and binding to a metal oxide surface.

In a process for preparing an alkylene glycol by reaction alkylene oxide with water in the presence of a catalyst of the present invention, a mixture of alkylene oxide and water in the liquid state is contacted with a catalyst containing a water tolerant Lewis acid having a non-coordinating or weakly coordinating anion and a rare earth or lanthanide cation. The process is carried out at a temperature from about 20° C. to 250° C., preferably 50° C. to 200° C. and a pressure greater than atmospheric, preferably 25 psig to 1000 psig with the temperature and pressure selected to maintain liquid phase conditions. The molar ratio of alkylene oxide to water is in the range from about 5 to 25.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1
Reaction of EO and Water in the Presence of Triflates:

EXAMPLE 1

A roundbottom flask was charged with 50 g of water (conductivity 18 mΩ) and chilled in an icebath. Ethylene oxide (EO) from Aldrich was introduced to the solution by bubbling EO gas from a lecture bottle through the solution. A total of 4.6 g of EO was introduced to the vessel. A sample was taken from the solution and analyzed by GC. The EO containing aqueous solution was transferred to a different roundbottom flask, which had been charged with 0.1404 g of scandium triflate [$Sc(CF_3SO_3)_3$] from Aldrich. The mixture of EO, water and $Sc(CF_3SO_3)_3$ was quickly transferred to a 100 mL autoclave. The reactor was pressurized to 50 psig with $N_2$ and heated up to 100° C., which took about 8 minutes. A sample was taken once the reactor had reached the target temperature and every 10 minutes thereafter to monitor the progress of the reaction. The samples were analyzed by off-line GC. During the initial heating ramp, 80% of the initial EO had reacted and the reaction was complete after 10 minutes at reaction temperature.

EXAMPLE 2

The procedure of Example 1 was followed except 20 mg of $Sc(CF_3SO_3)_3$ was used. The reaction was complete after 60 minutes.

EXAMPLE 3

The procedure of Example 1 was followed except the reaction temperature was set at 80° C. The reaction was complete in about 20 minutes at reaction temperature.

EXAMPLE 4

The procedure of Example 1 was followed except 10 g of EO and 50 g of water were used, while keeping the $Sc(CF_3SO_3)_3$ amount at 0.14 g. Even with the increased amount of EO, the reaction was still complete after only 10 minutes at reaction temperature.

EXAMPLE 5

The procedure of Example 1 was followed except 0.18 g of europium triflate [$Eu(CF_3SO_3)_3$] was used. About 85% conversion was observed after 60 minutes at reaction temperature.

EXAMPLE 6

The procedure of Example 1 was followed except 0.251 g of hafnium triflate [$Hf(CF_3SO_3)_4$] was used. At the end of the heating ramp, all EO had already been converted.

EXAMPLE 7

The procedure of Example 1 was followed except 0.17 g of yttrium triflate [$Y(CF_3SO_3)_3$] was used. About 75% conversion was observed after 60 minutes at reaction temperature.

EXAMPLE 8

The procedure of Example 1 was followed except 0.19 g of lanthanum triflate [$La(CF_3SO_3)_3$] was used. About 78% conversion was observed after 60 minutes at reaction temperature.

EXAMPLE 9

The procedure of Example 1 was followed except 0.192 g of ytterbium triflate [$Yb(CF_3SO_3)_3$] was used. About 85% conversion was observed after 60 minutes at reaction temperature.

Reaction of EO and Water in the Presence of Triflates (Group IIIA Cation):

COMPARATIVE EXAMPLE 1

The procedure of Example 1 was followed except 0.141 g of aluminum triflate [$Al(CF_3SO_3)_3$] was used. About 100% conversion was observed after only 10 minutes at reaction temperature.

COMPARATIVE EXAMPLE 2

A roundbottom flask was charged with 50 g of water (conductivity 18 mΩ) and 0.141 g of $Al(CF_3SO_3)_3$. The mixture of water and $Al(CF_3SO_3)_3$ was quickly transferred to a 100 mL autoclave. The reactor was pressurized to 50 psig with $N_2$ and heated up to 100° C. Once the mixture reached temperature, 4.6 g of EO was charged to the autoclave. A sample was taken 10 minutes after the EO was charged to the water catalyst mixture and analyzed by off-line GC. All EO had converted to glycols.

Reaction of EO and Water in the Presence of Triflates (Group IA Cation):

COMPARATIVE EXAMPLE 3

The procedure of Example 1 was followed except 51 mg of lithium triflate [Li(CF$_3$SO$_3$)$_3$] was used. About 73% conversion was observed after 60 minutes at reaction temperature.

Reaction of EO and Water in the Presence of Sulfate (Coordinating Anion):

COMPARATIVE EXAMPLE 4

The procedure of Example 1 was followed except 62 mg of scandium sulfate [Sc$_2$(SO$_4$)$_3$] was used. Full conversion was observed after 60 minutes at reaction temperature.

Reaction of EO and Water in the Presence of Chloride (Coordinating Anion):

COMPARATIVE EXAMPLE 5

The procedure of Example 1 was followed except 54 mg of scandium chloride [ScCl$_3$] was used. About 86% conversion was observed after 60 minutes at reaction temperature.

Reaction of EO and Water in the Presence of Acetate (Coordinating Anion):

COMPARATIVE EXAMPLE 6

The procedure of Example 1 was followed except 67 mg of scandium acetate [Sc(OAc)$_3$] was used. About 96% conversion was observed after 60 minutes at reaction temperature.

Reaction of EO and Water in the Presence of Nitrate (Coordinating Anion):

COMPARATIVE EXAMPLE 7

The procedure of Example 1 was followed except 81 mg of scandium nitrate [Sc(NO$_3$)$_3$] was used. Almost complete conversion was observed after 30 minutes at reaction temperature.

EO Hydration in the Absence of a Catalyst:

COMPARATIVE EXAMPLE 8

The procedure of Example 1 was followed except no catalyst was used. During the initial heating ramp, only 20% of the initial EO had converted, and even after 3 hours at reaction temperature, not all EO had converted as indicated by GC analysis. Only 70% conversion was observed.

The examples above with a catalyst having a Group IIIB, rare earth or Group IVB metal cation and a non-coordinating or weakly coordinating anion demonstrate the benefit and advantages of the present invention. Examples 1–9 show better conversion to EO over a shorter period of time compared to Comparative Example 8 (non-catalytic hydration). Examples 1–9 show conversion and reaction times that are at least as good as the prior art catalysts of Comparative Examples 1–3 (catalytic hydration with triflates and Group IA or Group IIIA cations). Examples 1–9 show conversion and reaction times that are better than the catalysts of Comparative Examples 4–7 (catalytic hydration with a Group IIIB cation and coordinating anions). Comparative Examples 4–7 show conversion and reaction times that are better than Comparative Example 8 (non-catalytic hydration). Based on these data, it is expected that a catalyst containing both a non-coordinating or weakly coordinating anion and a coordinating anion with a Group IIIB, rare earth or Group IVB metal cation would have better conversion and reaction time than that for non-catalytic hydration.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A process for the preparation of alkylene glycols comprising reacting an alkylene oxide with water in the presence of a catalyst of the formula MA$_x$ wherein M is a Group IIIB, rare earth metal, actinide or hafnium cation, A is a non-coordinating or weakly coordinating anion and x is the valence of M.

2. The process of claim 1 which additionally comprises reacting an alkylene oxide and with water in the presence of carbon dioxide.

3. The process of claim 1 wherein the alkylene oxides are of the formula R$^1$R$^2$(COC)R$^3$R$^4$, where each R$^1$, R$^2$, R$^3$ and R$^4$ is independently hydrogen or an alkyl of from 1 to 10 carbon atoms and the alkylene glycol is of the formula R$^1$R$^2$(COHCOH)R$^3$R$^4$.

4. The process of claim 2 wherein the alkylene oxides are ethylene oxide, propylene oxide or butylene oxide.

5. The process of claim 1 wherein the alkylene oxide is ethylene oxide and the alkylene glycol is ethylene glycol.

6. The process of claim 1 wherein M is selected from the group consisting of scandium, yttrium, lanthanum, europium, ytterbium, and hafnium.

7. The process of claim 6 wherein N is scandium.

8. The process of claim 1 wherein A is selected from the group consisting of a trifluoromethane sulfonate or triflate ([CF$_3$SO$_3$]$^-$), hexafluorophosphate ([PF$_6$]$^-$), [Al[OC(CF$_3$)$_3$]$_4$]$^-$, tetrafluoroborate ([BF$_4$]$^-$), perchlorate ([ClO$_4$]$^-$), teflate ([TeOF$_5$]$^-$), BArF ([B(ArH$_x$F$_y$)$_4$]$^-$ where Ar is an aryl and x+y=5), tosylate ([CH$_3$C$_6$H$_4$SO$_3$]$^-$), mesylate ([CH$_3$SO$_3$]$^-$) and antimonyhexafluoride ([SbF$_6$]$^-$).

9. The process of claim 8 wherein A is a triflate.

10. The process of claim 1 wherein the catalyst is scandium triflate [Sc(CF$_3$SO$_3$)$_3$], europium triflate [Eu(CF$_3$SO$_3$)$_3$], hafnium triflate [Hf(CF$_3$SO$_3$)$_4$], yttrium triflate [Y(CF$_3$SO$_3$)$_3$], lanthanum triflate [La(CF$_3$SO$_3$)$_3$] or ytterbium triflate [Yb(CF$_3$SO$_3$)$_3$].

11. The process of claim 1 wherein the process is carried out at a temperature from about 20° C. to 250° C.

12. The process of claim 11 wherein the temperature is 50° C. to 200° C.

13. The process of claim 1 wherein the process is carried out at a pressure greater than atmospheric.

14. The process of claim 13 wherein the pressure is 25 psig to 1000 psig.

15. The process of claim 1 wherein the molar ratio of alkylene oxide to water is in the range from about 5 to 25.

16. The process of claim 1 wherein the catalyst is homogeneous.

17. The process of claim 1 wherein the catalyst is heterogeneous.

18. The process of claim 17 wherein the catalyst is heterogenized on ion exchange resins, by microencapsulation or by being bond to a metal oxide surface.

19. A process for the preparation of alkylene glycols comprising reacting an alkylene oxide with water in the presence of a catalyst of the formula M'B$_x$ wherein M' is a Group IIIB, rare earth metal, actinide or hafnium cation, B is a coordinating anion and x is the valence of M'.

20. The process of claim 19 wherein M' is selected from the group consisting of scandium, yttrium, lanthanum, europium, ytterbium, and hafnium.

21. The process of claim 20 wherein M' is scandium.

22. The process of claim 19 wherein B is selected from the group consisting of nitrate ($[NO_3]^-$), sulfate ($[SO_4]^{2-}$, chloride ($[Cl]^-$) and acetate ($[CH_3COO]^-$).

23. The process of claim 22 wherein B is a nitrate.

24. The process of claim 19 wherein the catalyst is scandium sulfate $[Sc_2(SO_4)_3]$, scandium chloride $[ScCl_3]$, scandium acetate $[Sc(OAc)_3]$ and scandium nitrate $[Sc(NO_3)_3]$.

25. A process for the preparation of alkylene glycols comprising reacting an alkylene oxide with water in the presence of a catalyst of the formula $M''A_xB_y$ wherein M'' is a Group IIIB, rare earth metal, actinide or hafnium cation, A is a non-coordinating or weakly coordinating anion, B is a coordinating anion and x+y equals the valence of M''.

26. The process of claim 1 wherein M'' is selected from the group consisting of scandium, yttrium, lanthanum, europium, ytterbium, and hafnium.

27. The process of claim 26 wherein M'' is scandium.

28. The process of claim 25 wherein A is selected from the group consisting of trifluoromethane sulfonate or triflate ($[CF_3SO_3]^-$), hexafluorophosphate ($[PF_6]^-$), $[Al[OC(CF_3)_3]_4]^-$, tetrafluoroborate ($[BF_4]^-$), perchlorate ($[ClO_4]^-$, teflate ($[TeOF_5]^-$), BArF ($[B(ArH_xF_y)_4]^-$ where Ar is an aryl and x+y=5), tosylate ($[CH_3C_6H_4SO_3]^-$), mesylate ($[CH_3SO_3]^-$) and antimonyhexafluoride ($[SbF_6]^-$).

29. The process of claim 28 wherein A is a triflate.

30. The process of claim 25 wherein B is selected from the group consisting of nitrate ($[NO_3]^-$, sulfate ($[SO_4]^{2-}$), chloride ($[Cl]^-$) and acetate ($[CH_3COO]^-$).

31. The process of claim 30 wherein B is a nitrate.

32. The process of claim 25 wherein the catalyst is scandium triflate sulfate $[Sc(CF_3SO_3)(SO_4)]$, scandium triflate chloride $[Sc(CF_3SO_3)_2Cl]$, scandium triflate acetate $[Sc(CF_3SO_3)_2(OAc)_3]$ and scandium triflate nitrate $[Sc(CF_3SO_3)_2(NO_3)]$.

* * * * *